(12) United States Patent
Li

(10) Patent No.: US 7,979,109 B2
(45) Date of Patent: Jul. 12, 2011

(54) NEEDLE DRIVER FOR MAGNETIC RESONANCE ELASTOGRAPHY

(75) Inventor: Geng Li, Chai Wan (HK)

(73) Assignee: Lawrence Group Medical Device Trust, Reston, VA (US)

( * ) Notice: Subject to any disclaimer, the term of this patent is extended or adjusted under 35 U.S.C. 154(b) by 751 days.

(21) Appl. No.: 11/871,731

(22) Filed: Oct. 12, 2007

(65) Prior Publication Data

US 2008/0255444 A1 Oct. 16, 2008

Related U.S. Application Data

(60) Provisional application No. 60/851,644, filed on Oct. 12, 2006.

(51) Int. Cl.
*A61B 5/05* (2006.01)

(52) U.S. Cl. .................. 600/411; 600/410; 600/407

(58) Field of Classification Search ................. None
See application file for complete search history.

(56) References Cited

U.S. PATENT DOCUMENTS

| | | | |
|---|---|---|---|
| 4,154,228 A | 5/1979 | Feldstein et al. | |
| 5,095,910 A | 3/1992 | Powers | |
| 5,329,927 A | 7/1994 | Gardineer et al. | |
| 5,952,828 A | 9/1999 | Rossman et al. | |
| 5,967,991 A * | 10/1999 | Gardineer et al. | 600/461 |
| 5,977,770 A | 11/1999 | Ehman | |
| 6,673,086 B1 | 1/2004 | Hofmeier et al. | |
| 6,862,468 B2 * | 3/2005 | Smith | 600/410 |
| 7,034,534 B2 | 4/2006 | Ehman et al. | |
| 2003/0028094 A1 * | 2/2003 | Kumar et al. | 600/410 |
| 2006/0079773 A1 * | 4/2006 | Mourad et al. | 600/438 |

FOREIGN PATENT DOCUMENTS

EP 1429656 11/2005

OTHER PUBLICATIONS

R. Sinkus et al, "In-Vivo prostate MR-elastography", Proc. Intl. Soc. Mag. Reson. Med., 11:586 (2003).

Q. Chan et al, "Shear waves induced by moving needle in MR elastography", in Proceedings of the 26th Annual International Conference of the IEEE EMBS, San Francisco, CA, USA, pp. 1022-1024 (Sep. 1-5, 2004).

(Continued)

*Primary Examiner* — Unsu Jung
*Assistant Examiner* — Nigel Fontenot
(74) *Attorney, Agent, or Firm* — McHale & Slavin, P.A.

(57) ABSTRACT

The present invention is directed toward an acoustic, piezo-electric, electric, electro-mechanical or pneumatically driven surface drum driver, in mechanical engagement with a biopsy or acupuncture needle device and a method for its use for diagnosis of small e.g. 100 microns, tumors via the production of magnetic resonance elastographic images (MRE), without artifact production, in a magnetic resonance imaging (MRI) machine. In a second embodiment, the invention is directed toward an acoustically, pneumatically, piezoelectrically, electrically and/or electro-mechanically driven acupuncture needle, useful for simulating manual single-needle acupuncture treatments via a non-manually manipulated acupuncture needle; and further to a device and process for determination, using twin pneumatically driven surface drivers, of organ stiffness, e.g. brain stiffness, which can be quantified so as to be useful in elucidating and quantifying brain cognitive state, e.g. normal, mild cognitive impairment (MCI) or Alzheimer's dementia (AD).

3 Claims, 17 Drawing Sheets
(10 of 17 Drawing Sheet(s) Filed in Color)

| Subjects | MMSE | Mean Brain Stiffness (kPa) | |
|---|---|---|---|
| | | White Matter | Grey Matter |
| Normal | 28 | 6.799 | 2.585 |
| Normal | 26 | 7.824 | 2.842 |
| Normal | 30 | 8.978 | 2.345 |
| Normal | 24 | 7.235 | 2.399 |
| MCI | 20 | 5.611 | 2.081 |
| MCI | 21 | 6.393 | 2.633 |
| AD | 18 | 5.789 | 1.411 |
| AD | 15 | 5.223 | 2.065 |
| AD | 13 | 4.414 | 1.428 |
| AD | 14 | 4.180 | 1.202 |
| AD | 10 | 2.041 | 1.108 |

OTHER PUBLICATIONS

Q. Chan et al, "In-vivo Study: Needle driver in MR elastography", in Proceedings of the 2005 International Symposium on Quality of Bone and Scaffold Biomaterials Evaluated by microCT, pQCT and MRI, Hong Kong, Hong Kong, pp. 29-30 (Oct. 17-18, 2005).

Q. Chan et al, "Observation of anisotropic properties of skeletal muscle in MR elastography via a needle device", Proc. Intl. Sco. Mag. Reson. Med., 14:1704 (2006).

Q. Chan et al, "Localized application of shear waves to tissue for MR elastography via a needle device", Proc. Intl. Soc. Mag. Reson. Med., 13:2010 (2005).

Q. Chan et al, "Needle shear wave driver for magnetic resonance elastography", Magnetic Resonance in Medicine, 55:1175-1179 (2006).

Q. Chan et al, "Shear waves induced by needle or touch: an MRE study", in Proceedings of the Conference on Biomedical Engineering, Hong Kong, pp. 147-151 (Sep. 23-25, 2004).

G. Li et al, "Shear waves imaging induced by moving needle", in Proceedings of the 5th National MRI Academic Congress, Nanjing, China, pp. 157-159 (Oct. 15-18, 2004).

P. Rossman et al, Piezoelectric bending elements for use as actuators in MR elastography, Proc. Intl. Soc. Mag. Reson. Med., 11:1075 (2003).

E. Van Houten et al, "Initial in vivo experience with steady-state subzone-based MR elastography of the human breast", Journal of Magnetic Resonance Imaging, 17:72-85 (2003).

R. Muthupillai et al, "Magnetic resonance elastography by direct visualization of propagating acoustic strain waves", Science, 269(5232):1854-1857 (Sep. 1995).

Y. Zheng et al, "Magnetic resonance elastography with twin drivers for high homogeneity and sensitivity", Proc. of the 28th Intl. Conference of the IEEE-EMBS, New York, NY, USA (2006).

A. McKnight et al, "MR elastography of breast cancer: preliminary results", Am. J. Roentgenol., 178(6):1411-1417 (Jun. 2002).

R. Sinkus et al, "Imaging anisotropic and viscous properties of breast tissue by magnetic resonance-elastography", Magnetic Resonance in Medicine, 53:372-387 (2005).

R. Sinkus et al, "Viscoelastic shear properties of in vivo breast lesions measured by MR elastography", Magnetic Resonance Imaging, 23:159-165 (2005).

R. Muthupillai et al, "Magnetic resonance elastography", Nature Medicine, 2(5):601-603 (May 1996).

C. Lewa et al, "Viscoelastic property detection by elastic displacement NMR measurements", J. Magn. Reson. Imaging, 6(4):652-656 (Jul./Aug. 1996).

R. Sinkus et al, "High-resolution tensor MR elastography for breast tumour detection", Phys. Med. Biol., 45:1649-1664 (2000).

J. Lorenzen et al, "MR elastography of the breast: preliminary clinical results", Rofo, 174(7):830-834 (2002).

J. Lorenzen et al, "Menstrual-cycle dependence of breast parenchyma elasticity: estimation with magnetic resonance elastography of breast tissue during the menstrual cycle", Investigative Radiology, 38(4):236-240 (2003).

* cited by examiner

Protocol:
1. standard images
2. dynamic with CA
3. MRE

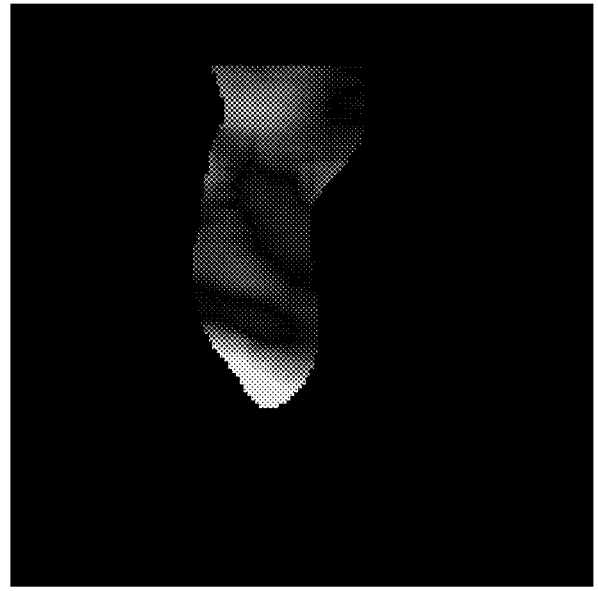
Rat
- Surface
- Needle
FIGURE 6

Rabbit
- Surface
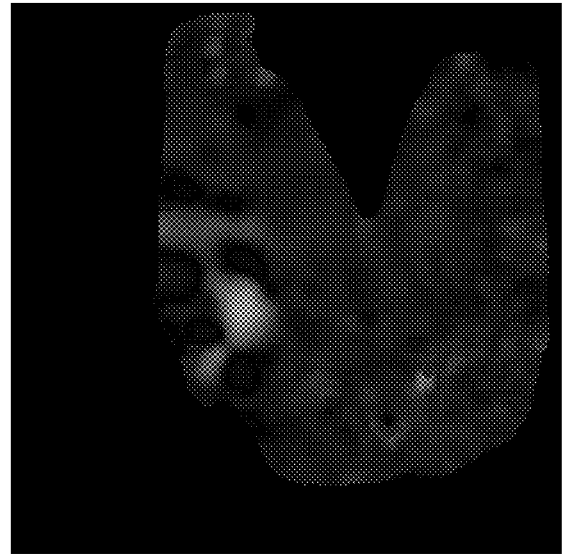
- Needle
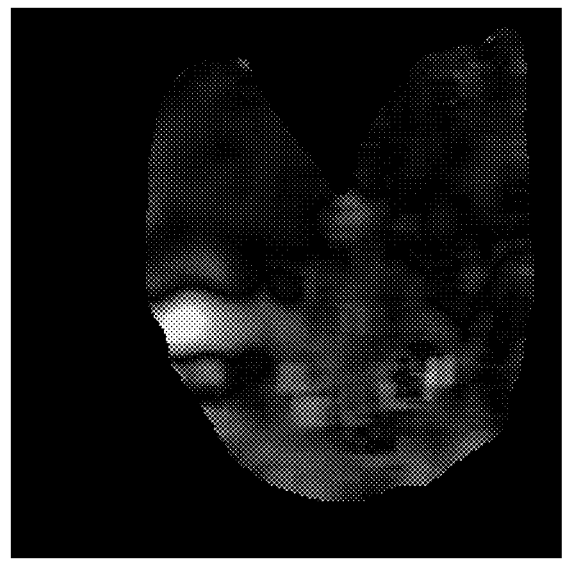
FIGURE 7

Human
- Surface
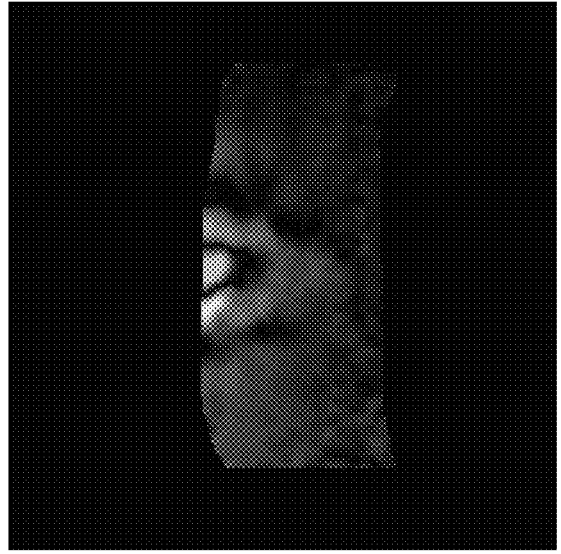
- Needle
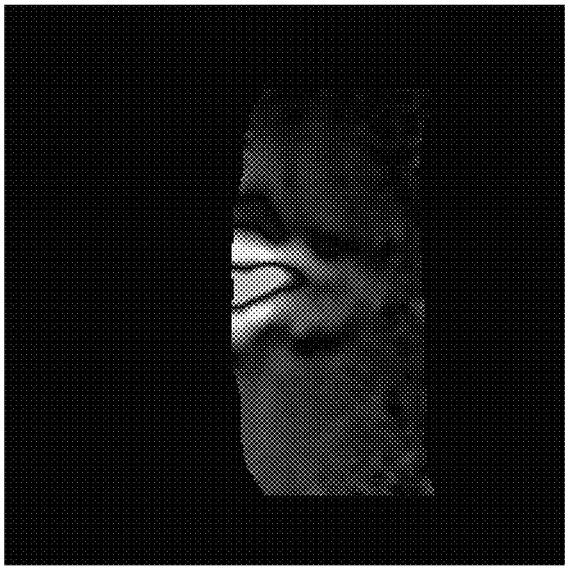
FIGURE 8

| Subjects | MMSE | Mean Brain Stiffness (kPa) | |
|---|---|---|---|
| | | White Matter | Grey Matter |
| Normal | 28 | 6.799 | 2.585 |
| Normal | 26 | 7.824 | 2.842 |
| Normal | 30 | 8.978 | 2.345 |
| Normal | 24 | 7.235 | 2.399 |
| MCI | 20 | 5.611 | 2.081 |
| MCI | 21 | 6.393 | 2.633 |
| AD | 18 | 5.789 | 1.411 |
| AD | 15 | 5.223 | 2.065 |
| AD | 13 | 4.414 | 1.428 |
| AD | 14 | 4.180 | 1.202 |
| AD | 10 | 2.041 | 1.108 |

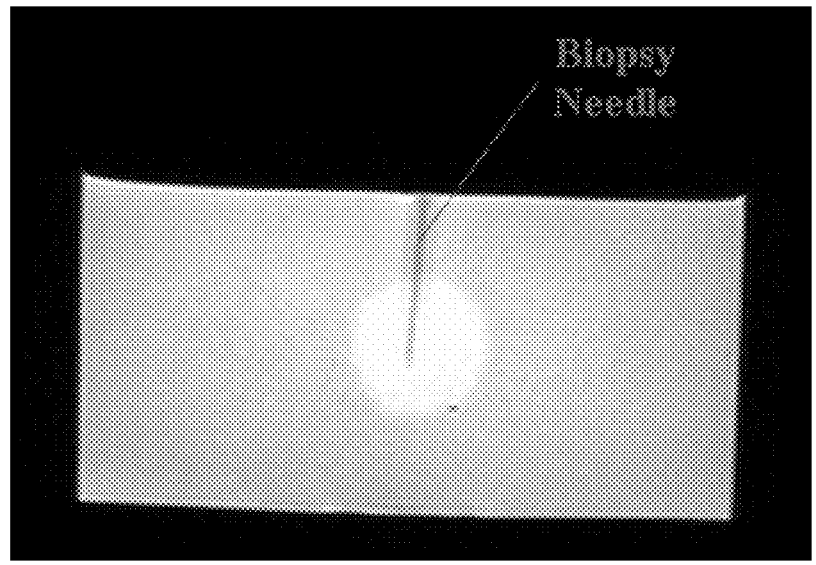
FIGURE 15
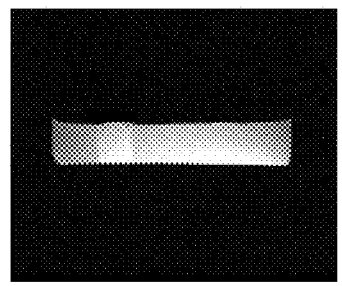     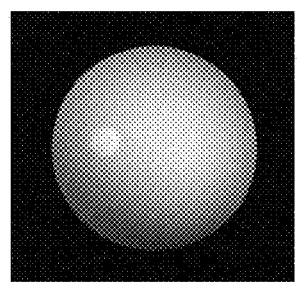
FIGURE 16A          FIGURE 16B

NEEDLE DRIVER FOR MAGNETIC RESONANCE ELASTOGRAPHY

CROSS-REFERENCE TO RELATED APPLICATIONS

This application claims benefit of the filing date of Provisional Application 60/851,644, filed on Oct. 12, 2006, the contents of which are herein incorporated by reference.

FIELD OF THE INVENTION

The inventions described herein relate to an apparatus for sensitive and specific detection of small tumors, e.g. about 100 microns, particularly within the breast, liver, kidney and prostate; and further relate to highly specific and sensitive methods for utilizing the apparatus in performing guided needle tissue biopsy, particularly biopsies of the breast, liver, kidney and prostate; and to use the needle driver as an electric acupuncture device; as well as to the use of twin pneumatic drivers for non-invasive analysis of brain stiffness as a method for diagnosing mild cognitive impairment (MCI) and Alzheimer's disease (AD).

BACKGROUND OF THE INVENTION

Breast cancer represents an internationally recognized public health concern, which often manifests itself in grave, and sometimes fatal, consequences for its victims. There is strong clinical evidence that breast cancer can be detected in its earliest stages, and that when found early, markedly improved results in morbidity and mortality are realized.

Mammography, clinical breast examination and breast self-examination are the current methods available for screening and early detection of breast cancer.

Mammography screening, although considered to be the "gold standard", nevertheless suffers from well-known limitations including over-diagnosis. With optimal technique and patient conditions, it has a reported sensitivity between 69% and 90% and a specificity between 10% and 40%.

Many factors, including density of breast tissue (i.e., younger patients, implants, and post surgical state) can affect these values. Mammography, when used alone, is believed to miss between 10% and 30% of all breast cancers. Possible reasons may include density of breast parenchyma (as mentioned above), poor technique and positioning, error by the reading radiologist, and slow growing breast cancers. Although certain strategies, such as computer-aided detection (CAD) and/or rereading by another radiologist, have been implemented in certain cases, to improve overall detection capability, their impact on detection of breast cancer is variable, at best. Because the specificity of mammography for characterizing breast lesions is relatively limited, typically 50-75% of the identified abnormalities, when removed for biopsy analysis, are found to be benign.

Ultrasound has been used as an adjunct to mammography, and is of particular value in differentiating cystic from solid lesions and in facilitating guided biopsy of suspicious areas. However, ultrasound has inherent limitations, including the possibility of missing micro calcifications (associated with ductal carcinoma in situ (DCIS)) and difficulty in ensuring that the entire breast is imaged with the transducer.

These limitations have prompted investigators to examine the value of other imaging modalities such as scintigraphy, contrast-enhanced MRI and Magnetic Resonance Elastography (MRE) for tumor detection and characterization.

Magnetic resonance (MR)-guided biopsy is a critical element of any breast MR imaging capability to ensure optimal patient management. The preponderance of studies has demonstrated that this technique has high sensitivity (90-100%) for detecting breast cancer. This exceeds the sensitivity of any other imaging technology. While multiple studies have established that the sensitivity of MR-guided biopsy for diagnosing breast malignancy approaches 100%, the reported diagnostic specificity has been generally less favorable, ranging between 65% and 80%. Therefore, further improvements in the diagnostic specificity of MR-guided biopsy for diagnosing breast cancer is essential to maximize early detection and treatment. Specifically, identifying other, independent parameters effective for characterizing MRI-accessible tissue will permit enhanced differentiation of malignancy from benign breast lesions.

Magnetic Resonance Elastography (MRE) is a new technique useful for assessing the viscoelastic properties of tissue. The MRE technique can quantitatively depict the elastic properties of, e.g. breast tissues in vivo and reveal the high shear elasticity in known breast tumors. Sinkus and colleagues described the inversion techniques for breast MRE and applied the methods to study the mechanical properties of breast tissues in normal volunteers and patients with breast cancer.

The most obvious potential role for MRE in breast imaging is as a possible method for improving the diagnostic specificity of contrast-enhanced MRI. In order to determine whether or not MRE-based measurements of shear stiffness can improve the specificity of lesion classification in CE-MRI of the breast, in vivo testing would need to be conducted.

The instant inventors have previously designed breast gel phantoms and a piezoelectric motor driven needle driver for needle-guided breast MRE; developed an animal model with breast tumors and made use of the MRE driver at GE 1.5T and 3T MRI system.

The present invention provides an improvement over this previous work which utilizes an enhanced, drum driven needle-guided breast biopsy device, which is particularly constructed and arranged for utilization within an MRI machine, to generate shear waves, necessary to perform highly sensitive and specific MRE analyses, without generation of artifactual interference, due to the non-metallic nature of the device. Tests of this device have been carried out on human subjects at MRI Research Lab, Mayo Clinic, Rochester, and Jockey Club MRI Centre, The University of Hong Kong.

The overall objective of such testing is to demonstrate the ability of the instantly disclosed drum driven needle biopsy device to reduce unnecessary biopsies and interventions, by virtue of its increased sensitivity and specificity in diagnosing invasive breast cancer, especially in women with high hereditary risk.

Both mammography and MRI-guided breast tumor biopsies have been performed for more than 25 years, but neither technique is able to elucidate small cancers.

The instantly designed devices are at the forefront of technology in breast cancer diagnostics. Given the very high resolution provided by MRE images, the MRE needle-guided breast biopsy technique can detect small cancers (MRE generates high-amplitude, artifact-free motion throughout a breast to enable visualization of tumors of less than one hundred microns, a very small tumor, which is unable to be found by either MR-guided biopsy or mammography. The end-result of this technology will be the saving of additional lives, along with a reduction in the number of un-wanted biopsy procedures.

MRE surface drivers have previously been used for the detection of breast, liver, kidney and prostate tumors via generation of spherical waves and piezoelectric bending element driven MRE needle drivers have been used for the detection of breast, liver, kidney and prostate tumors by the generation of plane waves.

Currently, MRE surface drivers have certain limitations. Since they use relatively low frequency, the wavelength is relatively longer. The long wavelength makes it difficult to detect smaller lesions. The instant needle driver utilizes a much higher frequency range; therefore the wave length induced by the needle driver is much shorter than that induced by the surface driver. Additionally, since the needle deeply penetrates the tissue, lesions which are deeply located, or are smaller in size, are able to be detected.

By combining a combination of either acoustic, piezoelectric, electric, electro-mechanical or pneumatically driven surface drum drivers along with corresponding needle drivers, it is possible to generate both spherical and plane waves at the same time. The combined drivers can further improve the shear waves and increase the sensitivity and specificity for the detection of tumors, while again reducing unnecessary biopsies. Simultaneously, it is possible to use the needle to perform biopsies immediately after finding the lesion, thus eliminating an additional invasive step.

The instantly disclosed technology can be used on a variety of MRI machines, including, but not limited to those manufactured by General Electric, Siemens and Philips.

COMPARISON OF TECHNIQUES

|  | MR-guided biopsy | MRE needle biopsy | MR + MRE |
|---|---|---|---|
| Specificity | 65-80% | 90% | 95% |
| Adverse reaction to Gd-DTPA | Yes | No | Yes |
| Sequence for specimen imaging | No | Yes | — |
| Needle size | larger | small | larger |
| Small cancer | undetectable | detectable | — |

DESCRIPTION OF THE PRIOR ART

Rossman et al, U.S. Pat. No. 5,952,828, discloses a device for applying an oscillatory stress to an object positioned in a polarizing magnetic field of an NMR imaging system used together to perform MR elastography. The devices employ electrically energized coils which are connected to drive members and drive plates in a manner to provide various oscillatory forces to an object being imaged. The different oscillatory forces enable different body organs to be imaged using MR elastography methods.

Ehman, U.S. Pat. No. 5,977,770, teaches a scan using an NMR imaging system that is carried out while applying an oscillating stress to an object being imaged. An alternating magnetic field gradient synchronized with the applied stress is employed in the NMR imaging pulse sequence to detect and measure synchronous spin motion throughout the field of view. The direction of the alternating gradient and/or the applied stress may be changed to measure and image the elastic properties of the object.

Feldstein et al., U.S. Pat. No. 4,154,228, discloses an arrangement for and method of inserting a glass microelectrode having a tip in the micron range into body tissue. The arrangement includes a microelectrode. The top of the microelectrode is attached to the diaphragm center of a first speaker. The microelectrode tip is brought into contact with the tissue by controlling a micromanipulator. Thereafter, an audio signal is applied to the speaker to cause the microelectrode to vibrate and thereby pierce the tissue surface without breaking the microelectrode tip. Thereafter, the tip is inserted into the tissue to the desired depth by operating the micromanipulator with the microelectrode in a vibratory or non-vibratory state. A mechanism including a second speaker is disclosed. Such mechanism is useful to sense tissue motion to control the microelectrode position with respect thereto substantially constant.

Gardineer et al., U.S. Pat. No. 5,967,991 discloses a disposable interventional medical device assembly for use with a color ultrasonic imaging system or other ultrasonic systems sensitive to motion. The assembly includes an interventional medical device having an elongated member for insertion into an interior region of a body under investigation, and piezo driver assembly coupled to the member of the interventional medical device. The driver assembly produces a vibratory oscillation which causes the member to exhibit a flexural motion in response thereto, the flexural motion having a zero amplitude point and a maximum amplitude point, wherein the driver assembly is coupled to the member at a point located between the zero amplitude point and the maximum amplitude point of the member's flexural motion. In one embodiment of the '991 patent, the interventional medical device can be a biopsy needle wherein the elongated member is the shaft of the biopsy needle. Also described is an ultrasonic imaging system which includes the earlier described disposable interventional medical device assembly and a scanner for detecting the flexural motion of the member of the disposable interventional medical device when the member is inserted into an interior region of a body under investigation. The system generates an image of the interior region of the body under investigation in which the flexural motion is locatively represented.

Gardineer et al., U.S. Pat. No. 5,329,927, discloses a VIBER vibrating mechanism which is coupled to a cannula or needle and operates to provide flexural vibrations to move the needle and to enable detection of the position of a needle within a body of interest by a color ultrasound imaging system. The VIBER mechanism exhibits multiple modes of oscillation when energized. The VIBER mechanism is excited to exhibit predetermined oscillations at a given frequency in the X plane, a predetermined oscillation at another frequency in the Y plane and still another frequency of oscillation in the Z plane. In this manner, the VIBER mechanism device exhibits motion in all three planes, which motion is detectable by a conventional color ultrasound imaging system. The frequency of oscillation is a function of the entire system, namely the VIBER mechanism, the needle or cannula which is attached to the VIBER mechanism and the tissue. The resonant frequency is preferred as it provides larger vibrational amplitudes. In this manner, a resonant frequency is controlled by means of a feedback control loop, whereby the frequency applied to the VIBER mechanism is monitored to determine resonance and is held at the resonant frequency as the VIBER mechanism or needle is moved. The vibration in the representative planes causes a typical conventional color ultrasound imaging system to display the vibration or movement by means of a color variation. By viewing the display, a system operator, such as a physician can visualize the location of the needle because of the color indication provided by the display.

Hofmeier et al., U.S. Pat. No. 6,673,086, discloses an apparatus for the micro-dissection of tissue with a fine needle, which is arranged on holder movable in space along three axes and the tip of which can be moved with the holder relative to the tissue, which is to be severed, wherein the needle is coupled with an oscillating drive mechanism, which causes the needle to oscillate in the longitudinal and/or transverse direction at a predetermined amplitude and frequency.

Powers, U.S. Pat. No. 5,095,910, discloses a system for imaging a biopsy needle with ultrasound is shown in which the needle tip elicits a Doppler response through controlled reciprocation of the needle tip. In a preferred embodiment the biopsy needle includes a hollow cannula which carries a removable stylet. Means for reciprocating the stylet is coupled to the proximal end of the stylet, and the distal tip of the stylet is reciprocated at the distal end of the cannula. This motion is detected through Doppler interrogation of the body region at which the biopsy is to be performed, and the Doppler response of the needle tip in the image of the body region allows the needle tip to be monitored as it approaches the tissue to be biopsied.

Smith, U.S. Pat. No. 6,862,468 is directed toward systems and methods for generating MRI elastographs within a blood vessel or organ. In a particular embodiment, (see col. 2, lines 31-35) an acoustic transducer and RF coil are placed upon a needle, which needle may be inserted in an organ, e.g. liver or brain, and an elastograph of the region is produced. This technique differs from the instantly disclosed surface drum driver, biopsy needle combination, in that the device of Smith is designed for total insertion of the acoustic transducer, RF coil and needle within the patient, e.g. within a vessel or organ, as opposed to insertion of only a thin needle as is instantly disclose, thereby substantially reducing artifactual interference; a technique neither taught nor suggested by Smith et al.

Ehman, U.S. Pat. No. 7,034,534, teaches a driver for use in applying an oscillating stress to a subject undergoing a magnetic resonance elastography (MRE) examination which includes a passive actuator located in the bore of the magnet and in contact with the subject. A remotely located acoustic driver for producing acoustic energy in response to an applied current, wherein this energy is coupled through a flexible tube to the passive actuator. A movable element in the passive actuator vibrates in response to this acoustic energy. Ehman fails to teach or suggest combining a biopsy or acupuncture needle with any type of driver, e.g. an electro-mechanical, acoustic or piezoelectric driver.

SUMMARY OF THE INVENTION

Needle biopsy is a medical test to identify the biological nature of a lump or mass, or other abnormal condition in the body. As previously stated, Magnetic Resonance Elastography (MRE) is a technique for assessing the viscoelastic properties of tissue, via a technique that images propagating mechanical waves using MRI. This is performed by synchronizing motion-sensitive MR imaging sequences with the application of acoustic waves in the 50 to 1000 Hz range We have treated alternative tissues such as the liver, brain and breast. Illustrative examples are included herein, which utilize MRE of breast and brain tissue as enabling, albeit non-limiting embodiment, for practicing the invention.

Breast MRE technique can quantitatively depict the elastic properties of breast tissues in vivo and reveal high shear elasticity in known breast tumors.

As an illustrative embodiment, the present invention provides a drum driven needle-guided breast biopsy device, constructed and arranged for utilization within an MRI machine so as to preclude generation of unwanted artifacts. Generation thereby of shear waves, enable the performance of highly sensitive and specific identification of lesions found in breast, liver, kidney and prostate tissues via Magnetic Resonance Elastography (MRE).

In one particular arrangement, the instant invention enables the combination of both surface and needle drivers for simultaneously producing spherical and plane waves, which results in a highly sensitive and specific test, and concomitantly leads to a reduction in the performance of unnecessary biopsies.

In an exemplary, albeit non-limiting embodiment, a surface driver can initially be used for the gross detection of possible tumor sites, and then a needle driver may be used to increase the sensitivity and specificity by providing an enhanced acoustic wave with a high degree of penetration. When very high shear wave tissue is found via this technique, which tissue is understood to have a higher probability of being a tumor, the needle driver can instantly function as a biopsy needle to reduce further invasive techniques and interventions, and to increase the sensitivity and specificity in diagnosing invasive breast, liver, kidney and prostate cancer.

In addition to the use of the needle driver of the present invention as a means for enhancing MRI diagnostic ability via the enablement of MRE elastographs of high sensitivity and specificity, the instant inventor has also determined that an acupuncture needle, when drivably engaged via one or more of an acoustic, pneumatic, piezoelectric, or electro mechanical driver mechanism, induce mechanical waves within the body tissue, and thereby provide a functionality, using a single needle, which closely resembles that induced manually by an acupuncturist. As opposed to presently available electrical acupuncture systems, which require at least two needles, so as to provide a positive and negative pole, the present device provides a non-manual acupuncture system which operates in a manner most similar to traditional manual acupuncture techniques.

It is understood that MRE uses a conventional MRI system to assess the elastic properties of tissues. To generate shear waves in tissue, there are differing types of drivers: a pneumatic driver, a piezoelectric driver, an electromagnetic driver, and the like, which in combination with any suitable wave generation means, can generate the types of spherical or planar waves necessary for diagnostic processes. When using a pneumatic driver, usually it is sufficient to place one driver at one location on the tissue. However, we have found that the shear wave generated by one pneumatic driver has difficulty in illuminating a large area like the whole brain or liver due to wave attenuation. In order to compensate for the wave attenuation, the instant inventors have further discovered that it is beneficial to use twin pneumatic drivers. It has been our experience that twin pneumatic drivers can compensate for the shear wave attenuation in phantom as well as in human brain.

It is therefore an objective of the instant invention to provide an MRE biopsy system which has much higher specificity and sensitivity than MR-guided biopsy.

It is another objective of the instant invention to provide a system which is a useful adjunct to contrast-enhanced MRI to diagnose and characterize breast cancers.

It is yet another objective of the instant invention to provide a system having a sequence for specimen imaging, so it can be used to make a confirmation for cancer tissue.

It is still another objective of the instant invention to provide a system which uses relatively small biopsy needles, in order to reduce the invasiveness and pain associated with the test.

It is yet an additional objective of the instant invention to provide a system to detect small cancers that cannot be found by other breast biopsy techniques.

It is yet a further objective of the instant invention to provide a non-manual acupuncture system, utilizing, either singly, or in any combination, acoustic, piezoelectric, pneumatic and electro-mechanical drivers for single acupuncture needles, whereby operation thereof provides vibratory stimulation in a manner most similar to traditional manual acupuncture techniques.

It is a still further objective of the instant invention to teach a method of accurately determining brain stiffness via the use of twin pneumatic drivers for the purpose of diagnosis, monitoring, elucidating the presence of early onset mild cognitive impairment and/or Alzheimer's disease, and to provide a non-invasive protocol for determining the progression and/or response of the condition to pharmacological intervention.

The overall objective of the invention remains the reduction of unnecessary biopsies and interventions, and providing increased sensitivity and specificity of MRE imaging, for diagnosing breast, liver, kidney, brain and prostate cancer; as well as the overall condition, as a function of organ stiffness, of a particular organ.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

The patent or application contains at least one drawing executed in color. Copies of this patent or patent application publication with color drawings will be provided by the Office upon request and payment of the necessary fee.

FIGS. 5-8 show comparative results obtained by MRE analysis using Needle and Surface drivers, for a Phantom target, Rat, Rabbit and Human tissues;

FIG. 15 shows a porcine gel phantom with a higher percentage porcine inclusion where the biopsy needle is inserted within he inclusion;

FIGS. 16A and 16B show respectively transverse and coronal images of the porcine gel phantom and inclusion of FIG. 15;

DETAILED DESCRIPTION OF THE INVENTION

Figure 1:
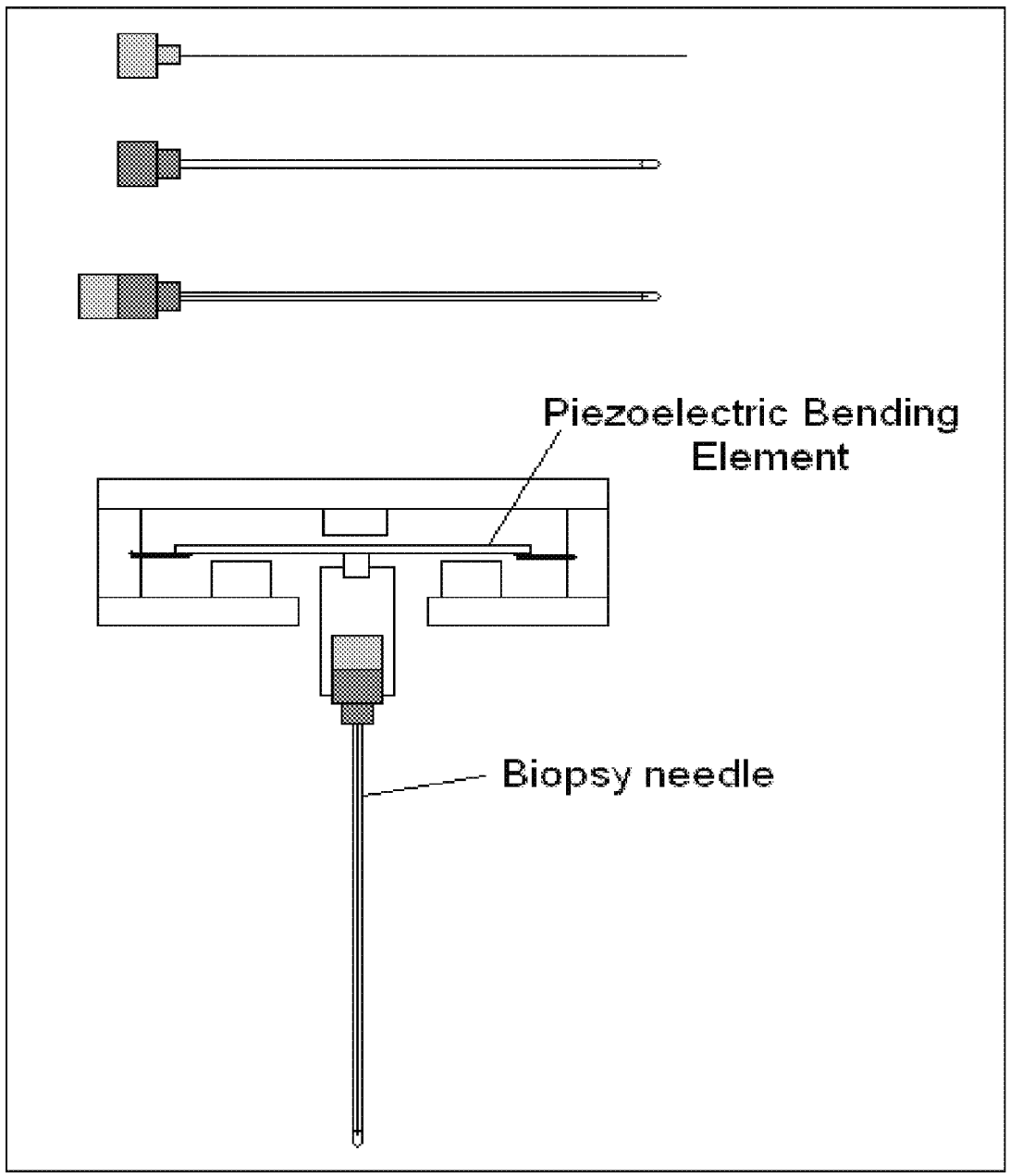
FIG. 1 shows a prior art mechanically driven biopsy device and associated needle system.
Figure 9:
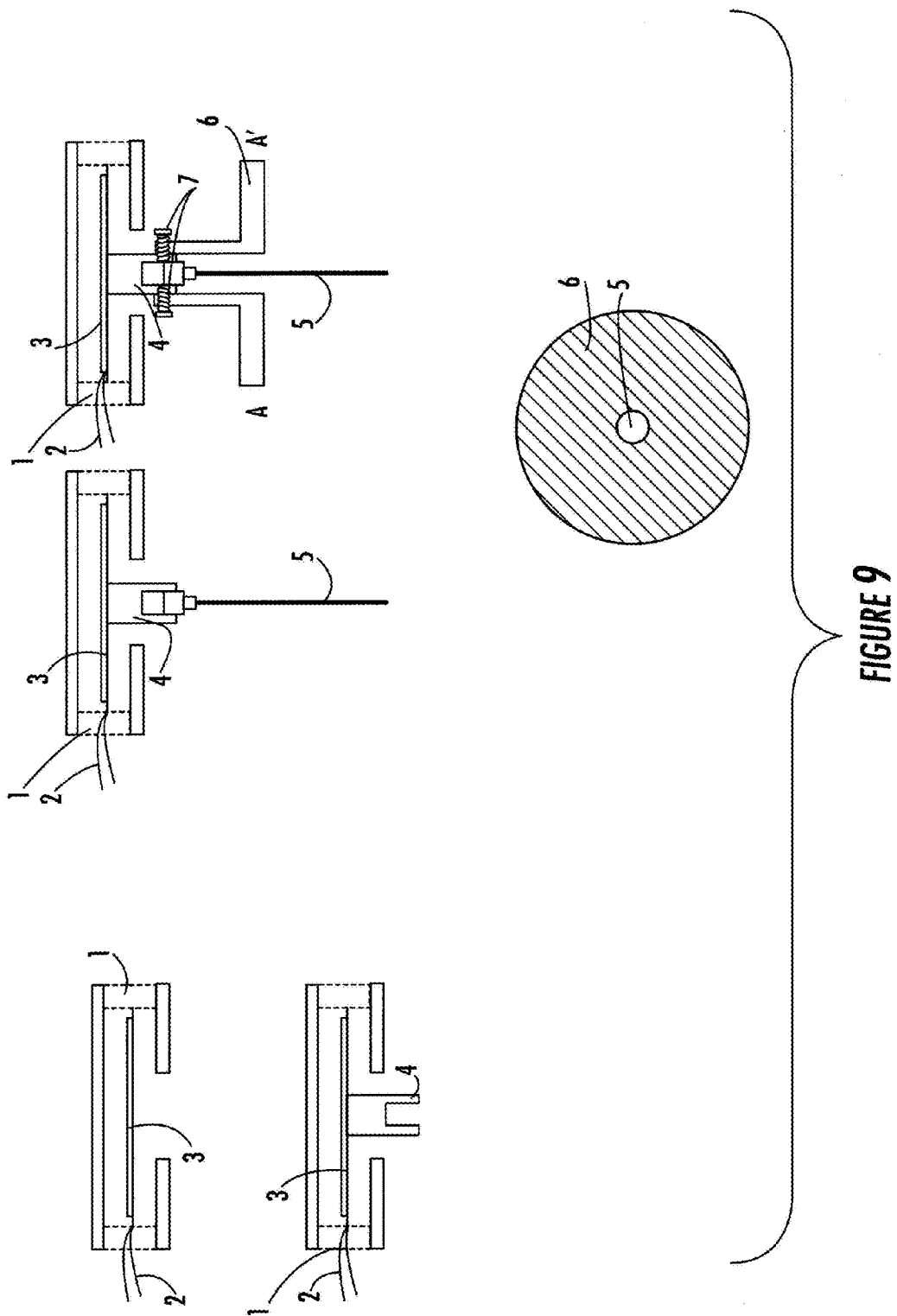
FIG. 9 references a cross-sectional view of a mechanically driven needle biopsy device and associated needle system.

FIGS. 1 and 9 reference a cross-sectional view of a mechanically driven needle biopsy device and associated needle system.

Figure 2:
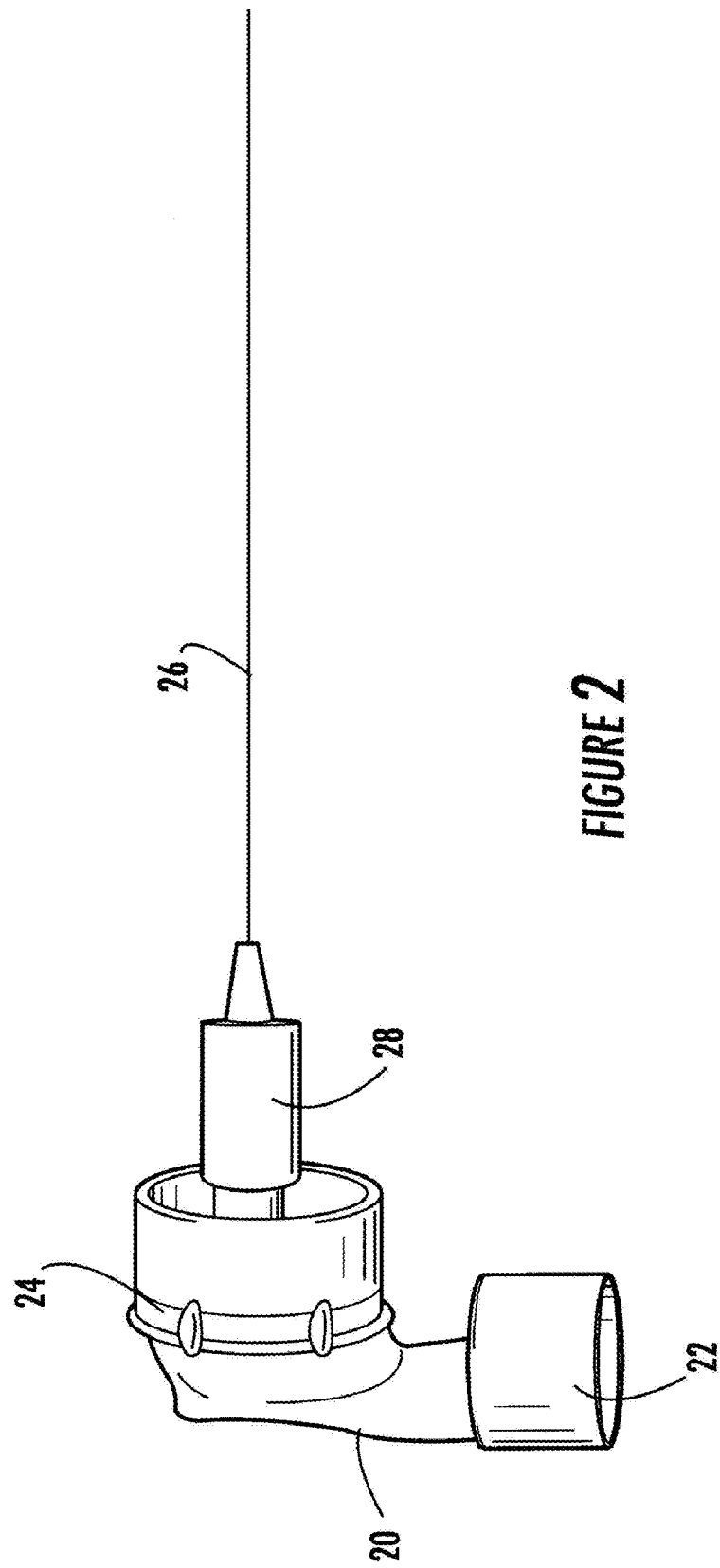
FIG. 2 shows a perspective view of a drum driver device and biopsy needle, for use in an MRI machine.

FIG. 2, is a perspective view of a drum needle driver embodiment, in accordance with the present invention, which can be used as a mechanical stimulus in MRE for producing a plane wave, as opposed to a spherical wave as is produced by a surface driver. The drum driver is formed from any polymer which is safe to use within an MRI machine, e.g. polycarbonate, high density polyethylene, polypropylene, ethylene-propylene copolymer, nylon, and the like. The drum needle driver includes a housing 20, which has an inlet end 22 for influx of a pulsatile flow of gas, e.g. air, nitrogen or the like, or the energy output supplied by an alternative wave generation means, e.g. a speaker (not shown) which impacts upon diaphragm 24, and causes a rhythmic undulation of the diaphragm 24, and a concomitant movement of the biopsy needle 26, which is in removable mechanical engagement with the diaphragm via a coupling member 28, at a frequency determined by the pulsatile frequency of the gaseous flow. The resulting MRE is able to yield a higher degree of accuracy in measurement of small tumors, e.g. 100 microns, by virtue of the enhanced specificity and sensitivity visible in the elastographic imaging resulting from the needle generated plane waves. A comparison of the imaging produced by the surface driver versus needle driver is shown in FIG. 5-8 for a phantom, rat, rabbit and human, respectively.

Figure 3:
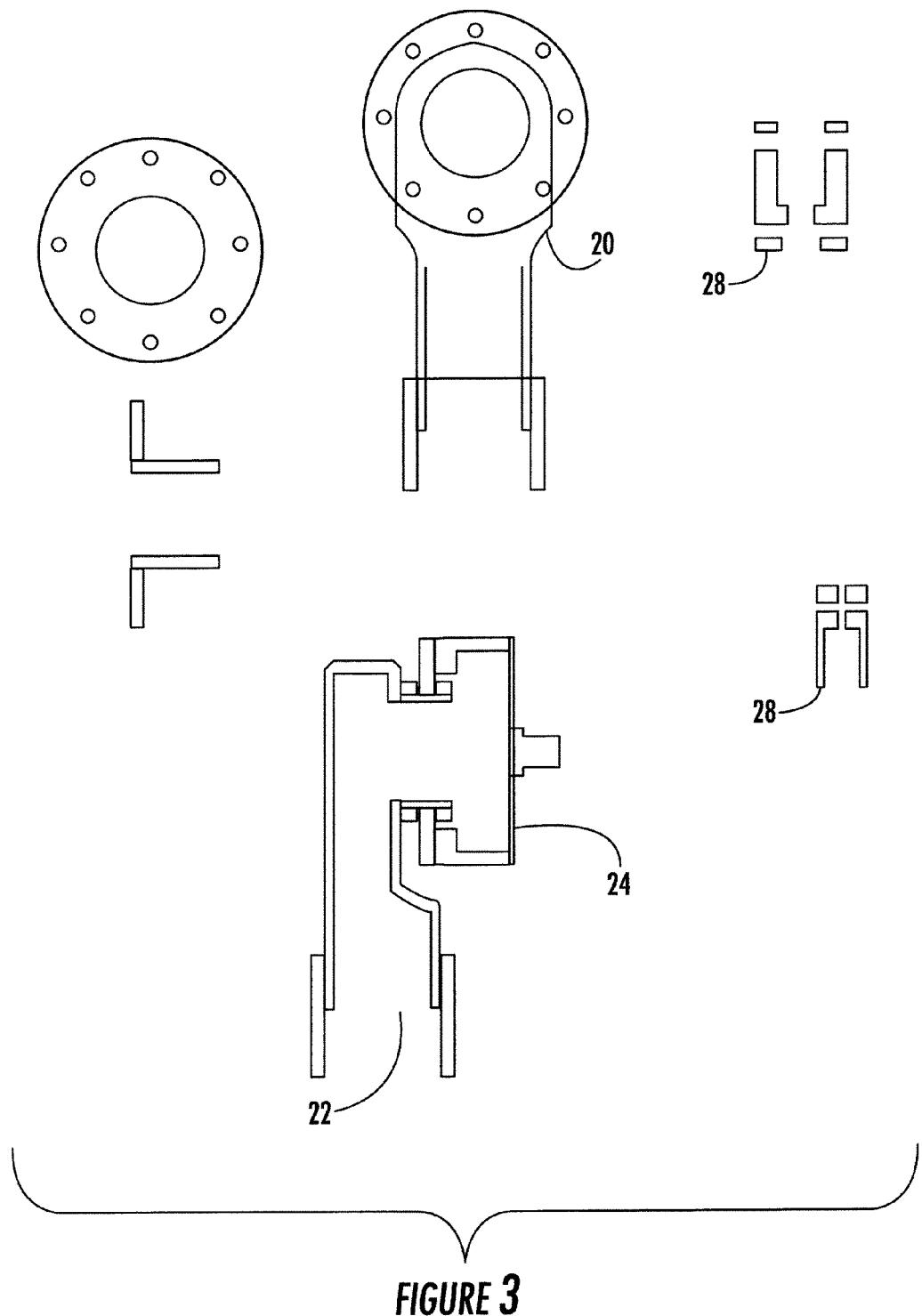
FIG. 3 shows alternative cross-sectional views of the drum driver device of FIG. 2.

FIG. 3 shows alternative cross-sectional views of the needle drum driver device of FIG. 2, which more specifically illustrate the diaphragm 24, housing 20, inlet for source of wave generator 22, and needle element holder 28.

As earlier alluded to, this technique can be employed for needle-guided biopsy in patients with breast, liver, kidney, brain and prostate tumors.

In a preferred, albeit non-limiting embodiment, a needle driver constructed and arranged for use within an MRI machine, and particularly constructed and arranged for performing needle-guided MRE biopsy is illustrated in FIGS. 2 and 3. A set of needles is provided (see FIG. 11) which are interchangeable, and may be selected as needed, specific to the particular tissue biopsy being performed. The needle driver produces plane acoustic waves orthogonal to the needle. In one embodiment, if desirable, an additional surface driver (see FIG. 4), may be added to produce waves normal to the point of contact and parallel to the needle. Both devices are suitable for MRE imaging, without production of unwanted artifacts, and the needle has an additional utility in that it can be used for biopsy.

Figure 4:
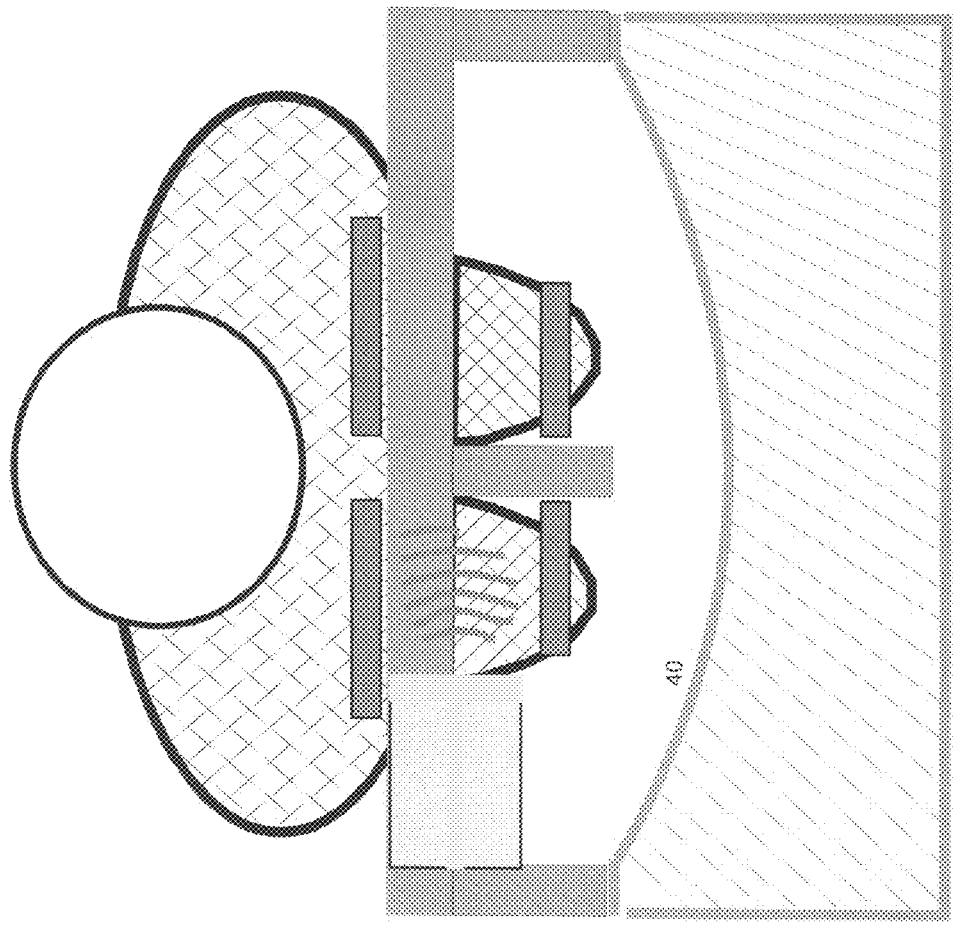
FIG. 4 shows an experimental setup for breast cancer MRE using the drum driver of FIG. 2.
Figure 5:
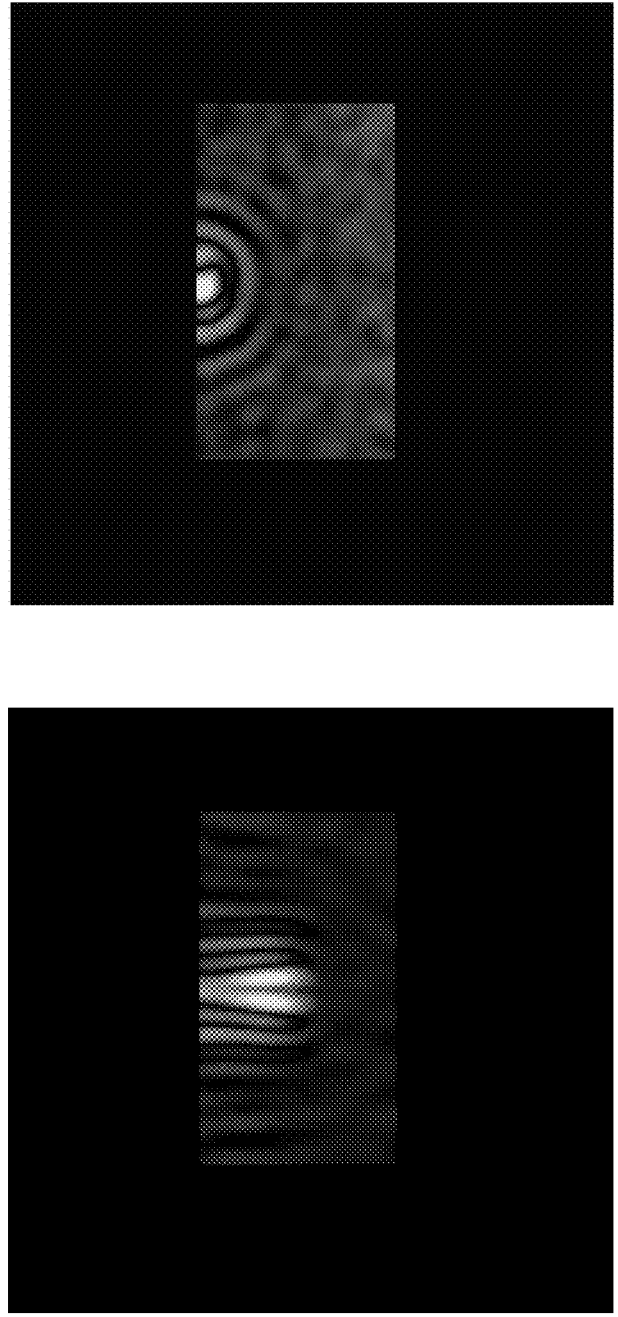

FIG. 4 shows a patient positioned within an MRI device (MRI device not shown) in an experimental setup for breast cancer MRE using a surface driver 42, wherein the pulsatile frequency of the drum driver (e.g. acoustic or pneumatic, or the like) is transmitted to the surface of the body, in this case the breast 40, to enhance the MRE image. Insertion of a needle drum driver, as illustrated in FIG. 2, is practiced wherein the needle is positioned parallel to the surface driver, to produce a sensitive imaging platform, absent artifacts, as described above.

The prior version of the invention provided a biopsy needle driver as shown in FIGS. 1 and 9. It consists of a piezoelectric bending element 3 for the vibration of the contact plate 6 and the needle 5. The surface (cross section at AA') 8a of the contact plate will attach to the skin of the subject for the surface vibration. The piezoelectric bending element 3 is held by the holder 1 and connects to power supply 2. A fixation 4 is attached to the center of the Piezoelectric bending element for holding the biopsy needle 5. A contact plate 6 for giving the vibration at the surface of skin is fixed to the fixation 4 by nylon screw 7. FIG. 9 also shows the cross section of the contact plate 9a at AA' from the top view.

Figure 10:
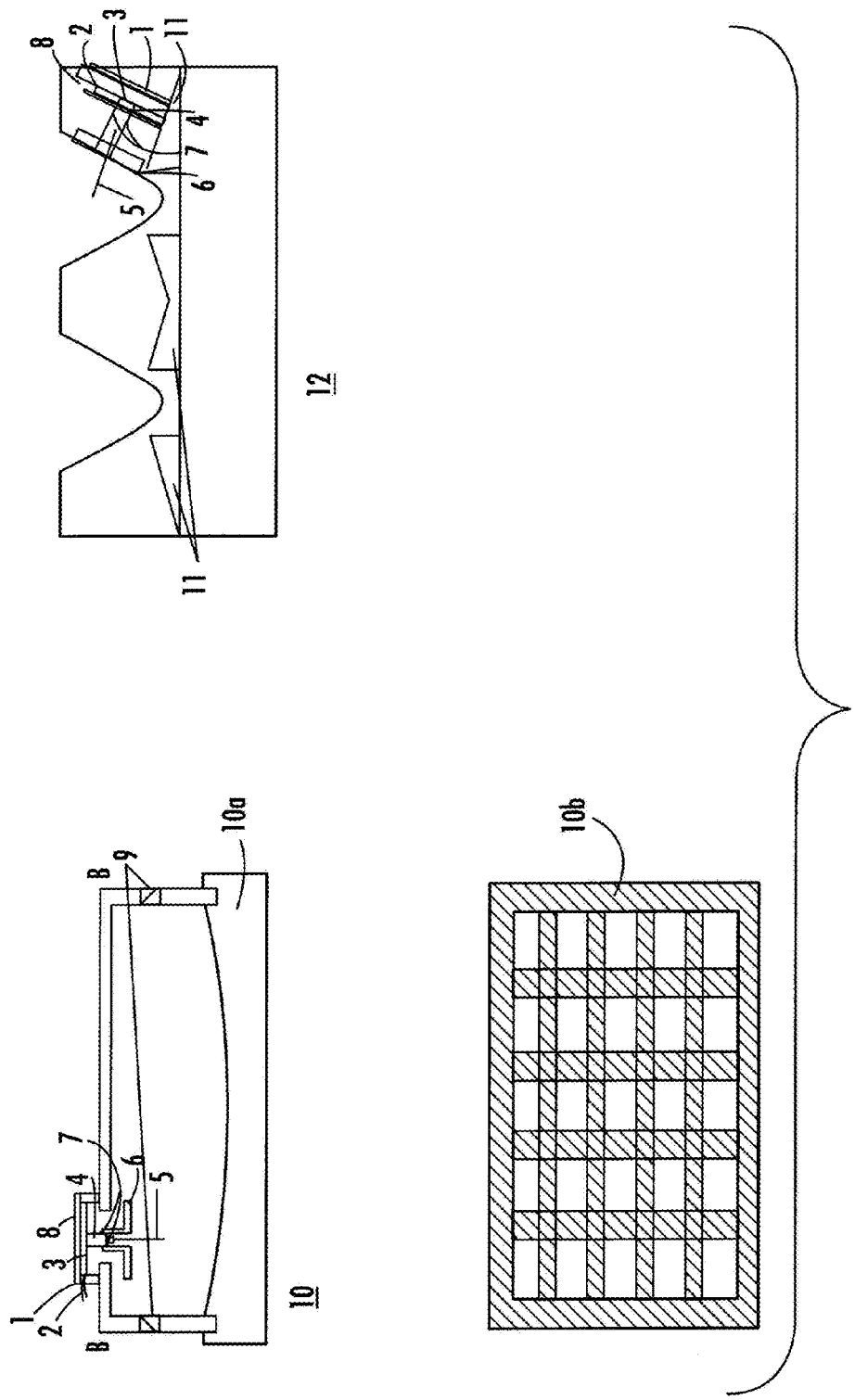
FIG. 10 shows a liver/kidney/prostate fixture and a breast fixture.

FIG. 10 shows a liver/kidney/prostate fixture 10 and a breast fixture 12. The patient lays supine for liver and prostate biopsy and lays prone for kidney and breast biopsies. Two knobs at each side of the liver/kidney/prostate fixture are used for adjusting the height of the fixture. The liver/kidney/prostate fixture is fixed to the table of MRI scanner 10a. Twenty holes 10b on the cross section from the BB' views are designated for the different locations of the liver/kidney/prostate in individuals. An inclined plane 11 for holding the needle driver can be put on the each side of the breasts according to the location of the lesion. The inclination angle of the inclined plane can be adjusted to fit in with the angle of biopsy needles.

Figure 11:
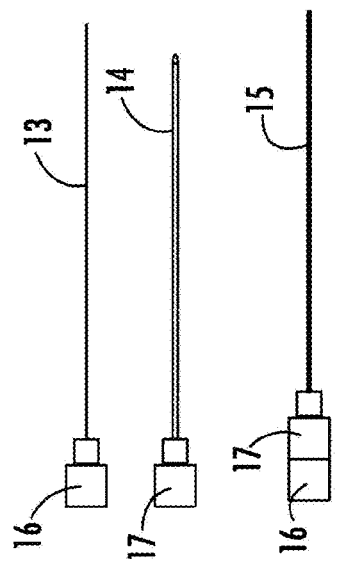
FIG. 11 shows a set of sample biopsy needles including an outer hollow needle and inner needle.

FIG. 11 shows a set of sample biopsy needles including an outer hollow needle 14 and inner needle 13. The handle 16 of the inner needle is attached to the proximal end 17 of the outer hollow needle to form the biopsy needle 15. An inner needle 13 is slid to engage within the lumen of outer hollow needle 14. There are 20 kinds of biopsy needle available with different inner diameters (12, 14, 16, 18 and 20 gauge) and different lengths (10, 13 16 and 20 cm).

Figure 12:
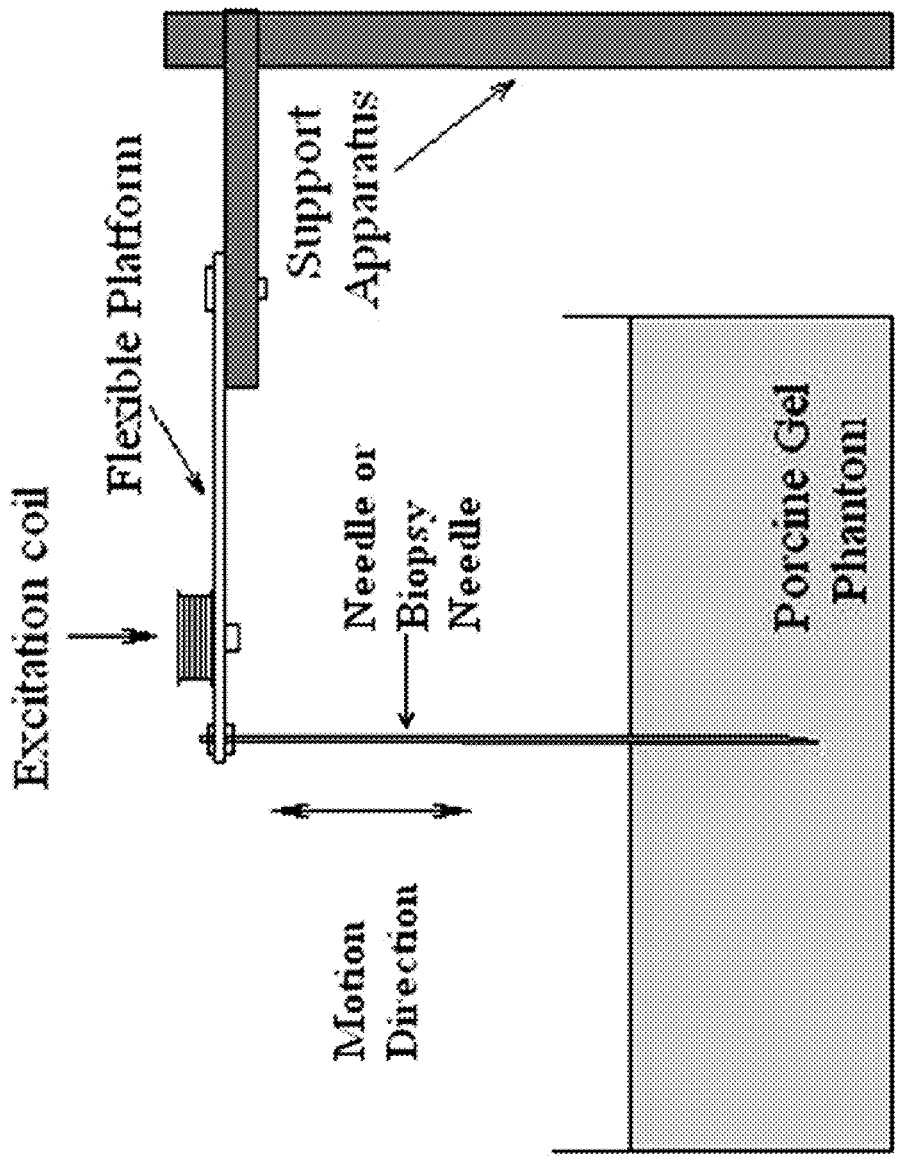
FIG. 12 shows an electro-mechanically driven acupuncture or biopsy needle.

FIG. 12 shows an electro-mechanically driven acupuncture or biopsy needle. Using this technique, or the acoustically, pneumatically or piezoelectrically driven embodiments outlined herein, induced waves by a moving needle can be generated, thereby simulating the up and down movement of physical acupuncture treatment. One could then evaluate the induced waves of simulated acupuncture via MRE, to thereby study, in vivo, the efficacy of various acupuncture techniques.

ADDITIONAL EXAMPLES

Human Brain Study

Comparison of the Brain Stiffness Among Normal Subject, MCI Patient and AD Patient Using Magnetic Resonance Elastography with Twin Drivers using the 3T GE MRI systems in Beijing Neurosurgical Institute.

Study Purpose

To develop a new technique based on the state-of-the-art in Magnetic Resonance Elastography (MRE) for early detection and diagnosis of Mild Cognitive Impairment (MCI) and Alzheimer's Disease and for establishing a standard range of brain viscosity and elasticity in normal subjects, MCI patients and AD patients.

Methods

Figures 13A, 13B, 13C, 14:
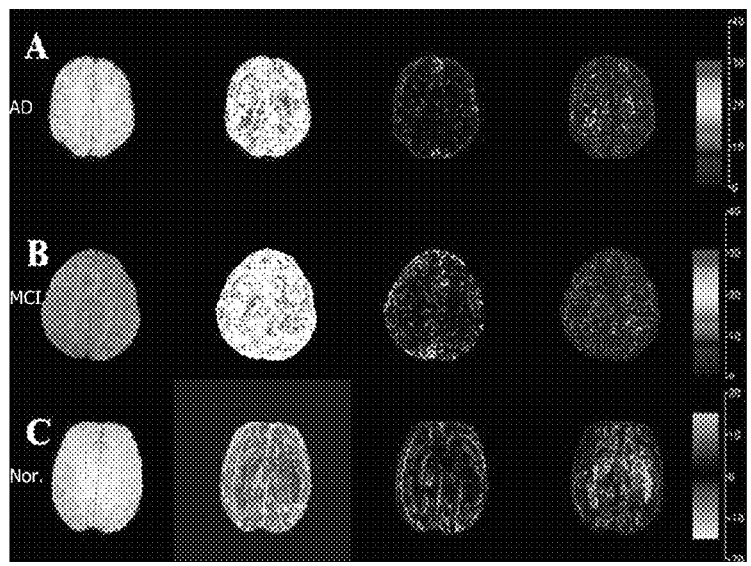
FIGS. 13A, 13B and 13C show the results of MRE using twin pneumatic drivers on normal (13C), MCI (13B), and AD (13A) patients.
FIG. 14 show relative brain stiffness for subjects suffering from various mental impairment versus normal subjects.
Figures 17A, 17B, 17C, 17D:
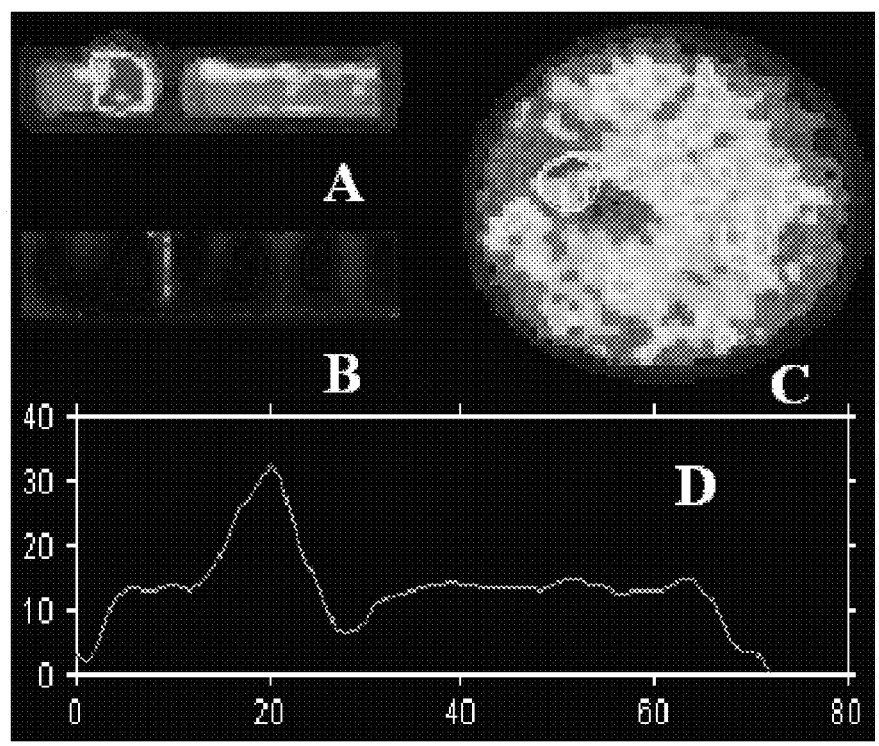
FIGS. 17A, 17B, 17C and 17D depict transverse stiffness images using the biopsy needle driver (A); Transversal wave images using the biopsy needle driver (B); Coronal stiffness images using the biopsy needle driver (C), (the area in the white circle is the inclusion); the profile of stiffness of the phantom with inclusion (green lines) (D).

As illustrated in FIGS. 13C, 13B and 13A respectively, MRE brain images of 4 normal subjects, 2 MCI (mild cognitive impairment) and 5 AD (Alzheimer's dementia) patients were obtained using a GE 3 T MRI scanner. A commercial brain coil was used in the 3T GE MRI systems in Beijing Neurosurgical Institute. Mechanical oscillation was produced by a homebuilt transducer. Typical excitation frequency for in vivo measurements was 40 Hz. The pulse generator was triggered via the standard trigger output channel of the spectrometer. The different components of the mechanical wave were measured using the modified spin-echo pulse sequence developed by Mayo Clinic. MREview developed in Mayo Clinic was used for data acquisition and reconstruction.

More specifically, it is generally only necessary to utilize a single pneumatic driver. However, when illuminating a large organ, such as the brain, the shear wave generated by one pneumatic driver is insufficient to illuminate the whole area due to wave attenuation. In order to compensate for the wave attenuation, we have found it useful to use twin pneumatic drivers. We have determined that the use of twin pneumatic drivers can compensate for the shear wave attenuation propagated when illuminating a human brain with a single pneumatic driver.

In practice, a speaker drives air which propagates in an attached tube connected to the driver. The membrane of the driver is placed on the skull and vibrates to generate a shear wave propagating in the brain. The drum-like driver and tubes are made of plastic and are safe for use in the MRI device.

We place two pneumatic drivers symmetrically on the both sides of the skull. The two pneumatic drivers are driven synchronously by the same source. When comparing the wave pattern images at a particular frequency, e.g. 100 Hz excitations, generated by a single pneumatic driver and twin pneumatic drivers respectively, we have observed that the shear wave generated by a single pneumatic driver exhibits unacceptable attenuation. In both cases, the pneumatic drivers are driven at the same frequency and same power. The twin pneumatic drivers generate an interference wave pattern which can compensate the attenuation effectually. A stiffness value is generated from these data (see for example FIG. 14).

Results

Compared with normal subjects (FIG. 13C), the brain stiffness of both white matter and grey matter is lower in MCI patients (FIG. 13B). Also the brain stiffness is lower in AD patients (FIG. 13A) than in MCI patients (FIGS. 13 and 14). The technique is potentially valuable for early detection and diagnosis of MCI and Alzheimer's disease. In addition, the technique provide a pathway for understanding the pathology of the disease, monitoring disease progression and testing the effects of drug treatment.

CONCLUSIONS

The data demonstrates that the MRE technique is highly valuable for early detection and diagnosis of Alzheimer's disease and for understanding its pathology, monitoring disease progression and effectiveness of drug treatment. Also, it may provide greater hope for MCI patients for the prevention of the development of AD, since, at a very early stage, MCI is reversible or can be slowed pharmacologically, wherein there is currently no effective pharmacological intervention for AD.

Tumor Detection in Rabbit

MRE is a phase contrast imaging technique to quantitatively measure the elasticity of tissues. Typically, an oscillating driver is placed on the surface to generate the shear waves. In measuring depth penetration of the shear wave in MRE, such measurement is limited by attenuation. Referring to FIGS. 15,16A and 16B, the instant inventors utilized a biopsy needle as the driver to detect the 15% porcine gel inclusion in a 10% porcine gel phantom which simulates a tumor in tissues as well as in the model of rabbit with tumor in vivo. It is shown that the biopsy needle driver can accurately measure the stiffness and location of the tumor. An additional benefit is that the biopsy procedure may be carried out at the same time.

Many lives can be saved when human have routine X-ray, CT or MRI examinations of the breast, liver and kidney that can detect breast, liver and kidney cancer in its earliest, most curable stages. However, most of the abnormalities seen on those techniques are not cancer. The most common practice to make a diagnosis is to perform a biopsy in which a sample of tissue is removed from the breast/liver/kidney for analysis. In the past, it required surgical operation that was painful and disfiguring. Today, interventional radiologists often can make a diagnosis without surgery with a technique called needle biopsy. In this technique, an ultrasound needle is used to remove small samples of tissue from the breast. It is less painful, much less disfiguring (there is no scar, MRI guided core biopsy left a large scar in the biopsy region) and requires a shorter recovery time than surgical biopsy, but the specificity is low.

The present inventors have designed a needle driver for needle-guided breast, liver and kidney MRE in human subjects. The overall objective is to reduce the unnecessary biopsies and interventions, and increase the sensitivity and specificity in diagnosing invasive breast, liver and kidney cancer. The purpose of this study was to justify whether shear waves caused by an inserted biopsy needle can accurately detect and locate the position of tumors.

Materials and Methodology

Driver Design

The electromechanical driver with a biopsy needle is shown in FIG. 12. The biopsy needle (COOK MRE) was 0.73 mm diameter and MRI compatible. One side of the needle is fixed to the driver and the other side of the needle is inserted into the phantom. The amplified sinusoidal signal was input into the excitation coil. Then signal was synchronized to the image sequence and triggered by the pulse sequence. The alternative current creates a magnetic field which is perpendicular with the main magnetic field. This causes oscillation along the vertical direction. The oscillating motion will be transmitted to the phantom by the needle and the propagating shear wave is observed.

Design of Phantom:

10% porcine gel phantom was used in the experiment to simulate the tissue. A cylindrical 15% porcine phantom of 20 mm diameter was included in the phantom to simulate the tumor as shown in FIG. 15.

In-Vivo Animal Study:

A female New Zealand white rabbit (6 months old, 4.2 kg) was used in this study. Animal research ethics approval was obtained and the institute's guidelines for the care and use of laboratory animals were observed. A VX2 hepatocarcinoma lump with the volume of 1 cm×1 cm×1 cm was implanted into the left thigh muscle 15 days before the experiment to grow for the tumor. The rabbit was anesthetized with the mixture of Ketamine 10% (at dose of 150 mg/kg, ALFASAN, Woerden-Holland) and XYLAZINE 2% (ALFASAN, Woerden-Holland) at 2:1.

Measurement:

The experiment was done in a Philips Intera Achiva 3T system with SENSE Flex-M surface coil. MRE uses a phase-contrast technique to image the shear wave. The MRE sequence also uses motion sensitizing field gradients which are synchronized to the propagating waves. The Field Of View (FOV) is 160 mm. Matrix size is 80×80. TE/TR=25 ms/243 ms. Slice thickness is 2 mm. We set the excitation frequency at 150 Hz. The stiffness of the phantom is calculated using the equation: $\mu=\rho f^2 \lambda^2$ where $\rho$ is the density of the phantom, f is the excitation frequency of the driver and $\lambda$ is the shear wavelength measured from the wave images.

TABLE 1

Stiffness Value of the inclusion and background
Mean ± Standard Deviation (kPa)

|  | Inclusions | Background |
|---|---|---|
| Biopsy needle | 19.05 ± 2.53 | 12.88 ± 1.42 |

FIGS. 17A, 17B, 17C and 17D depict transverse stiffness images using the biopsy needle driver (A); Transversal wave images using the biopsy needle driver (B); Coronal stiffness images using the biopsy needle driver (C), (the area in the white circle is the inclusion); the profile of stiffness of the phantom with inclusion (green lines) (D).

Figure 18A:
FIGS. 18A, 18B and 18c show the T2, T1W and T1W STIR images respectively of a rabbit leg with a biopsy needle inside the tumor lesion.
Figure 18B:
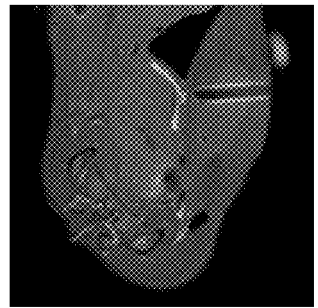
Figure 18C:
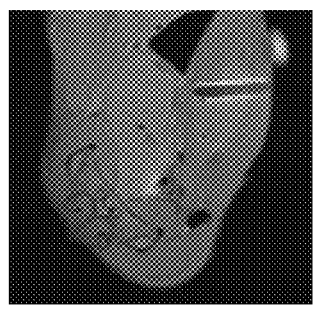
Figure 19A:
FIGS. 19A and 19B respectively depict an anatomy image of a rabbit leg with tumor and an elastogram of a rabbit muscle with tumor.
Figure 19B:
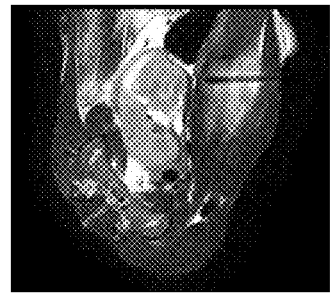
Figure 20:
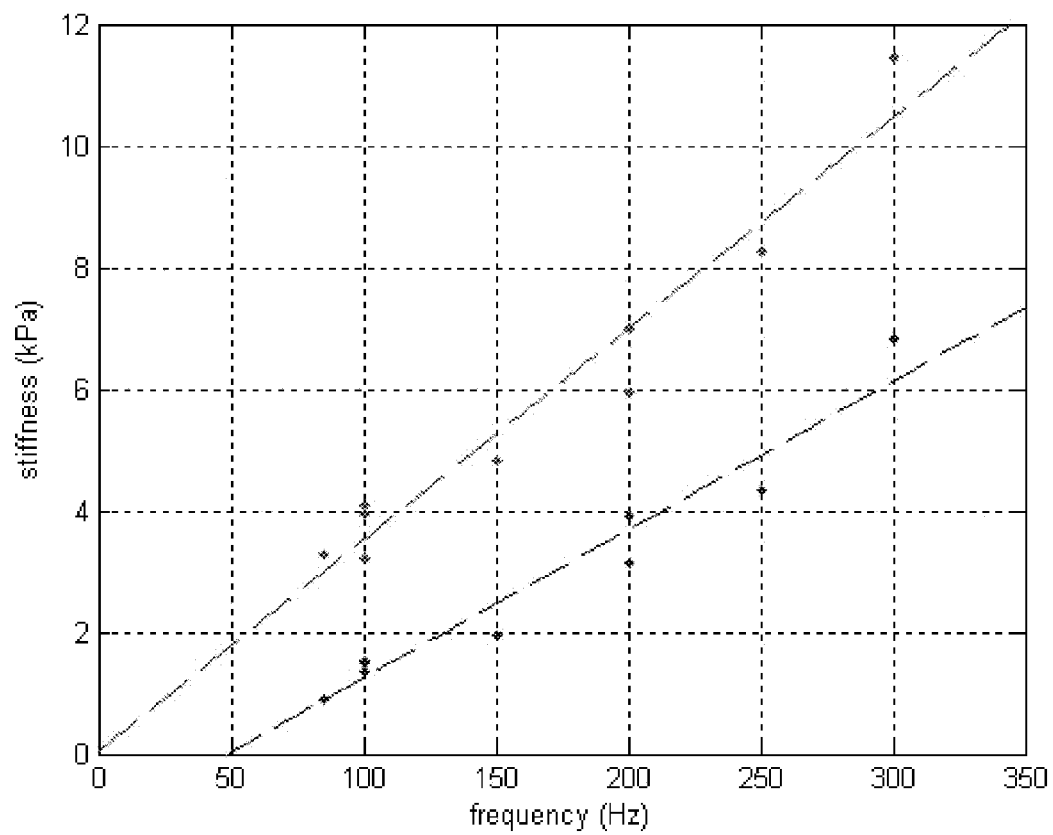
FIG. 20 is a graph of Stiffness value under different frequency, wherein the upper line represents stiffness of tumor and the lower line represents stiffness of normal muscle.

FIGS. 18A, 18B and 18c show the T2, T1W and T1W STIR images respectively of a rabbit leg with a biopsy needle inside the tumor lesion;

FIGS. 19A and 19B respectively depict an anatomy image of a rabbit leg with tumor and an elastogram of a rabbit muscle with tumor;

FIG. 20 is a graph of Stiffness value under different frequency, wherein the upper line represents stiffness of tumor and the lower line represents stiffness of normal muscle

TABLE 2

Stiffness Value of the tumor and muscle
Mean ± Standard Deviation (kPa)

|  | Tumor | Muscle |
|---|---|---|
| Biopsy needle | 3.62 ± 1.83 | 1.03 ± 0.22 |

DISCUSSION AND CONCLUSION

The experimental result shows that the vibrating biopsy needle can generate propagating waves to differentiate phantoms with different densities and the phenomenon is observed in MRE in this experiment. Traditionally, surface drivers are used to generate shear waves. However, the shear wave produced by the surface driver may attenuate significantly before reaching the deeper tissues. By using the biopsy needle, this difficulty can be overcome and we can measure the stiffness of tissues in deep location. Another merit of the biopsy needle is that we can directly use it to sample the abnormalities for further analysis on a desired site by making use of the MRE image. This technology can be used for needle-guided biopsy in patients with breast, liver and kidney lesions.

In addition to the experiment with phantom, we have performed in-vivo animal study. FIG. 18 A-C show the T2W and shear wave images with the biopsy needle inserted into the leg of normal rabbit at 100 Hz. The result illustrates that the biopsy needle driver can provide a clear propagating wave pattern in the muscle of rabbits. FIG. 19 A-B shows the T2W image and elastogram with the biopsy needle inserted into the leg with tumor at 85 Hz. Table 2 shows the stiffness value of the tumor and muscle. The distance between the needle and the edge of the tumor is 5 mm. From the elastogram, we can clearly see the tumor region has higher stiffness value than the muscle. The location of the tumor can be easily identified. Thus the biopsy needle as MRE driver can be a good tool to precisely detect and localized tumors.

It is intended that the specification, drawings and examples can be considered as exemplary only, with the true scope and spirit of the invention being indicated by the following claims. It should be understood that only the preferred embodiments have been shown and described and that all changes and modifications that come within the spirit of the invention are desired to be protected.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process to establish a standard range of brain viscosity and elasticity in normal subjects, Mild Cognitive Impairment (MCI) patients and Alzheimer's Disease (AD) patients comprising:
    positioning a patient within a magnetic resonance imaging (MRI) device;
    providing a pair of pneumatic drum drivers useful within said MRI device, each driven synchronously by a single wave generator;
    positioning said pair of pneumatic drum drivers in contact with the patient's skull, thereby simultaneously generating a shear wave, and a corresponding interference wave effective to neutralize attenuation of said shear wave, each wave propagating in the brain;
    elucidating brain stiffness data as a function of shear wavelength; and
    establishing a standard range of brain viscosity and elasticity in normal subjects, MCI patients and AD patients;
    and correlating changes in brain viscosity and elasticity between normal, MCI and AD patients.

2. A process for generating magnetic resonance elastographs of cancerous tumors comprising:
    positioning a patient within a magnetic resonance imaging (MRI) device;
    providing a first acoustic, piezoelectric, electric, electromechanical or pneumatically driven surface drum driver, useful within said MRI device, in mechanical engagement with a biopsy or acupuncture needle;
    providing a second acoustic, piezoelectric, electric, electro-mechanical or pneumatically driven surface drum driver in contact with said patient, in an area adjacent said acupuncture or biopsy needle;
    inserting said biopsy or acupuncture needle within a tissue suspected of containing a cancerous tumor;
    providing wave generating means for synchronous movement of said biopsy or acupuncture needle within said tissue, wherein both spherical and plane waves are generated, thereby enhancing specificity and sensitivity; and
    generating a magnetic resonance elastograph.

3. The process of claim 2, further including the act of conducting a biopsy by use of the biopsy needle.

* * * * *